(12) United States Patent
Sands

(10) Patent No.: US 11,185,175 B2
(45) Date of Patent: Nov. 30, 2021

(54) SELF-CATHETERIZATION ASSISTANCE SYSTEM

(71) Applicant: Diane Elizabeth Sands, Winthrop, MA (US)

(72) Inventor: Diane Elizabeth Sands, Winthrop, MA (US)

(*) Notice: Subject to any disclaimer, the term of this patent is extended or adjusted under 35 U.S.C. 154(b) by 0 days.

(21) Appl. No.: 16/948,392

(22) Filed: Sep. 16, 2020

(65) Prior Publication Data

US 2021/0076848 A1    Mar. 18, 2021

Related U.S. Application Data

(60) Provisional application No. 62/901,402, filed on Sep. 17, 2019.

(51) Int. Cl.
| | |
|---|---|
| *A47G 1/02* | (2006.01) |
| *A47G 1/06* | (2006.01) |
| *F16M 11/12* | (2006.01) |
| *F16M 11/28* | (2006.01) |
| *A61M 25/01* | (2006.01) |

(52) U.S. Cl.
CPC .............. *A47G 1/02* (2013.01); *A47G 1/0622* (2013.01); *F16M 11/126* (2013.01); *F16M 11/28* (2013.01); *A61M 25/01* (2013.01); *A61M 2202/0496* (2013.01); *A61M 2205/583* (2013.01); *A61M 2205/587* (2013.01)

(58) Field of Classification Search
CPC .............. A61M 25/01; A61M 25/0017; A61M 2205/583; A61M 2205/587; A61M 2210/167; A61M 2210/1092; A61M 2202/0496; A47G 1/02; A47G 1/0622; A45D 42/10; A45D 42/16; A61B 5/0079; G02B 25/02; G02B 7/002

See application file for complete search history.

(56) References Cited

U.S. PATENT DOCUMENTS

| 4,933,822 A | * | 6/1990 | NakaMats | ............... | F21S 6/003 |
| | | | | | 362/282 |
| 5,311,366 A | * | 5/1994 | Gerace | ................. | A61B 5/0079 |
| | | | | | 248/476 |

(Continued)

*Primary Examiner* — Nathan R Price
*Assistant Examiner* — Anh Bui
(74) *Attorney, Agent, or Firm* — Dunlap Bennett & Ludwig, PLLC; Anna L. Kinney

(57) ABSTRACT

A self-catheterization assist device is provided. The self-catheterization assist device includes an adjustable support component; a yoke attached to the adjustable support component; a mirror surround rotatably attached to the yoke; a dual-sided mirror with a flat surface and a concave surface mounted within the mirror surround; and an independently repositionable focused-beam lamp mounted on the mirror surround. A self-catheterization assist kit is also provided. The kit includes a visual aid device and a urine containment bowl. The visual aid device has an adjustable support component; a yoke attached to the adjustable support component; a mirror surround rotatably attached to the yoke; a dual-sided mirror with a flat surface and a concave surface mounted within the mirror surround; and an independently repositionable focused-beam lamp mounted on the mirror surround. The urine containment bowl is attachable to the adjustable support component.

10 Claims, 6 Drawing Sheets

(56) References Cited

U.S. PATENT DOCUMENTS

| | | | |
|---|---|---|---|
| 7,921,478 B1* | 4/2011 | Vanini | E03D 9/00 |
| | | | 4/300.3 |
| 9,304,285 B2 | 4/2016 | Barbour et al. | |
| 2015/0062729 A1* | 3/2015 | Barbour | F16M 1/00 |
| | | | 359/875 |
| 2015/0265031 A1* | 9/2015 | Roett-OConnor | A45D 42/10 |
| | | | 132/288 |
| 2017/0164719 A1 | 6/2017 | Wheeler | |
| 2020/0352774 A1* | 11/2020 | Rabinowitz | A61F 5/453 |

* cited by examiner

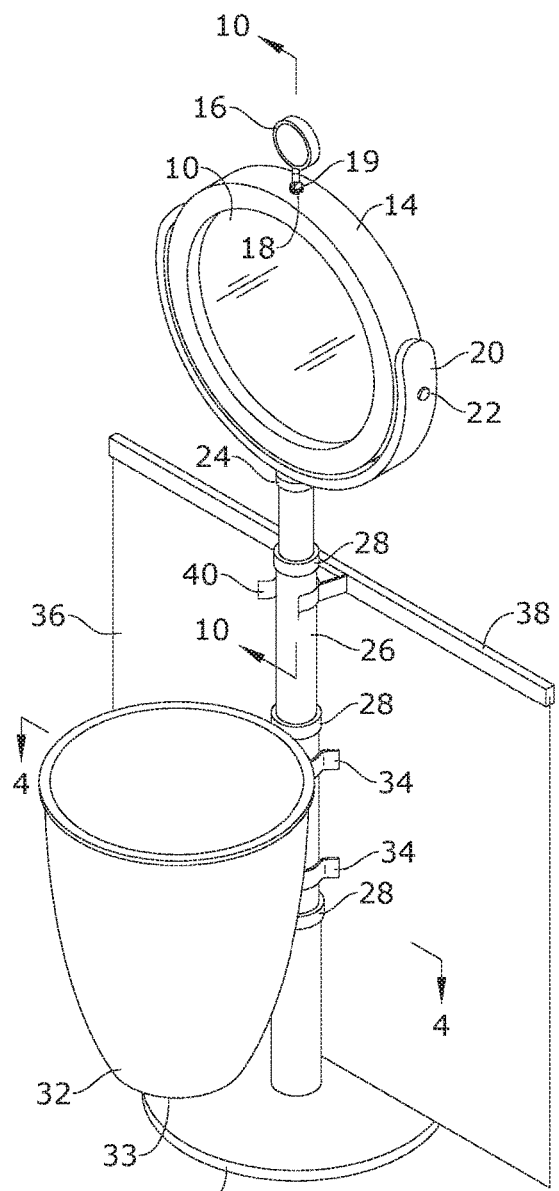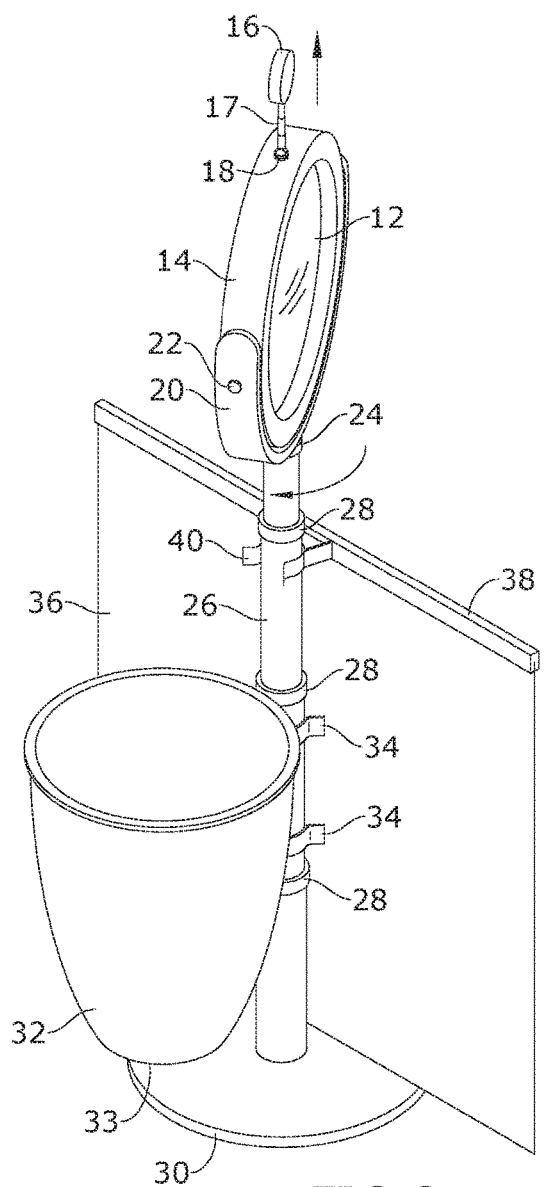

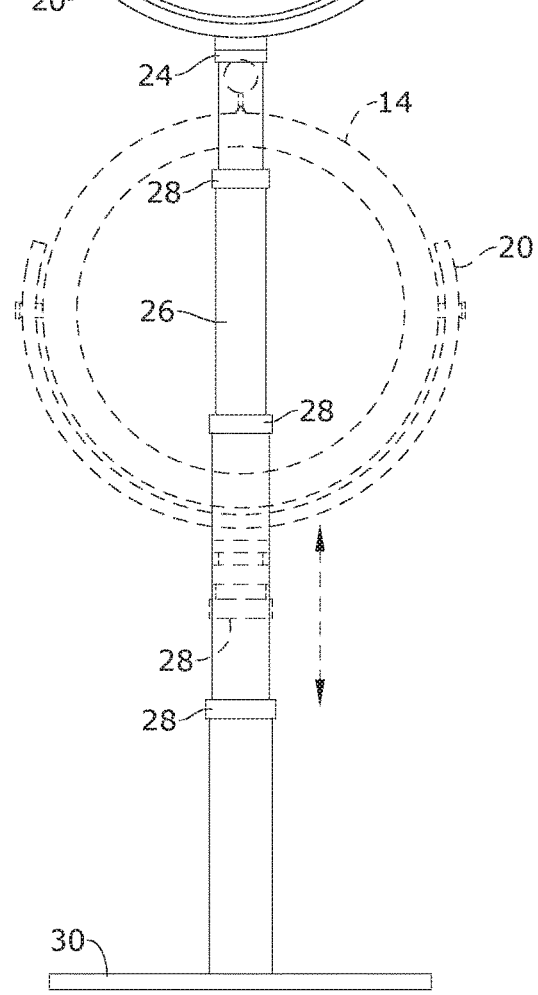
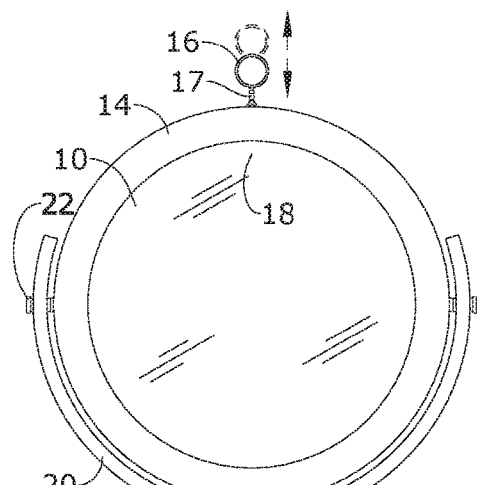
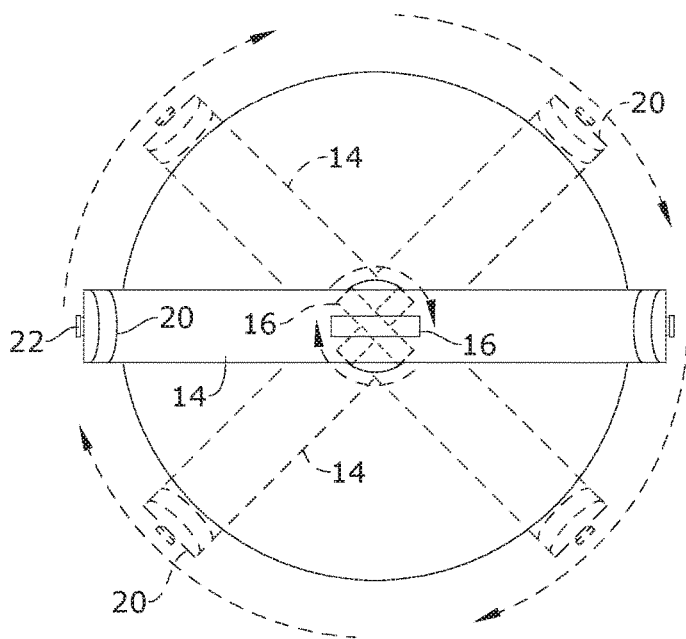
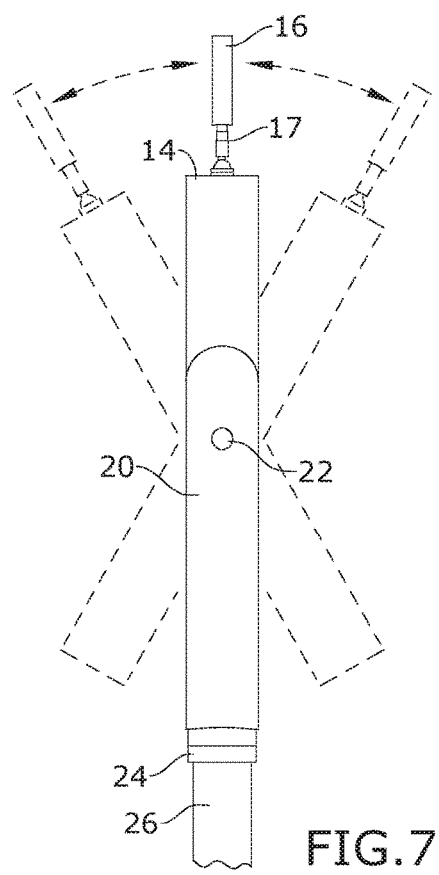
FIG.5
FIG.6
FIG.7

SELF-CATHETERIZATION ASSISTANCE SYSTEM

CROSS-REFERENCE TO RELATED APPLICATION

This application claims the benefit of priority of U.S. provisional application No. 62/901,402, filed Sep. 17, 2019, the contents of which are herein incorporated by reference.

BACKGROUND OF THE INVENTION

The present invention relates to a device to assist self-catheterization and, more particularly, to a device that provides containment and splatter protection.

Patients needing catheterization when in the hospital are frequently sent home with instructions to self-catheterize. Self-catheterization is a much more difficult task for women than it is for men. Proper placement is very important, since catheterization may result in serious infection if not done properly. The patient often requires the assistance of a second person, including help with lighting, positioning, imaging, and finding anatomical locations. Without assistance, proper placement is difficult if not impossible. Moreover, self-catheterization can be extremely messy, as urine flow may begin without warning and may splatter extensively.

The is no product currently on the market to address these problems. The only device currently commercially available to assist self-catheterization is a small, index card-sized mirror that attaches to the thighs and is not sufficiently visible to anatomically assist with this procedure.

US 2017/0164719 to Wheeler discloses a lit, waterproof, telescoping, collapsible mirror for personal hygiene. The Wheeler device does not at all address urine flow and does not provide a magnifying mirror. Moreover, the Wheeler device does not allow the user to independently direct the mirror and the light source, such as a high-intensity LED focused beam, to adequately visualize the vulva for proper self-catheterization, creating extensive risk of bacterial contamination and danger for infection and sepsis.

U.S. Pat. No. 9,304,285 to Barbour et al. is drawn to a collapsible, tripod-mounted mirror and light for use in self-catheterization. The Barbour et al. device does not at all address urine flow and the tripod likely can only be used by a woman in limited positions. The tripod shown in Barbour is large, cumbersome, heavy, and unmanageable by a disabled or neurologically impaired person. The user would need assistance to transport the device. The Barbour device lacks a magnifying mirror and the battery-powered light is unlikely to provide sufficient illumination, leaving the user vulnerable to the risk of bacterial contamination and infection.

U.S. Pat. No. 5,311,366 to Gerace is drawn to a mirror assembly mountable on a person's legs for use in self-catheterization. The Gerace assembly does not at all address urine flow and does not allow the user to independently direct the mirror and the light source to adequately display the vulva for proper self-catheterization. In fact, the light source is optional and is unlikely to provide sufficient illumination, leaving the user vulnerable to the risk for contamination and infection.

As can be seen, there is a need for a hands-free device to assist self-catheterization that provides an adjustable reflective surface with ample lighting to make the reflected vulva easily visible in a variety of positions, provides urine containment, and provides splatter prevention.

The present invention provides a device operative to assist a person to self-catheterize independently and/or at home. This device obviates the need for a second person to assist with an additional pair of hands. The invention may be placed between a user's legs or attached to the thighs, leaving the user's hands free to assist with anatomical location. The present invention also provides a kit including the inventive mirror device as well as an attachable bowl for containment and a splatter screen for cleanliness.

The device of the present invention addresses the issues associated with independent or disabled catherization in a home or non-medical environment. It may be used by the elderly, neurologically impaired, and those who are disabled, as well as normally abled and weakened people. The user may self-catheterize in an independent environment and remain in their home in a safe, clean, and healthy living environment.

The inventive device may also be used for crafting and use of small tools for other tasks.

SUMMARY OF THE INVENTION

In one aspect of the present invention, a self-catheterization assist device is provided, comprising an adjustable support component; a yoke attached to the adjustable support component; a mirror surround rotatably attached to the yoke about a first rotational axis; a dual-sided mirror mounted to the mirror surround; and an independently repositionable focused-beam lamp mounted on the mirror surround.

In another aspect of the present invention, a self-catheterization assist kit is provided, comprising a visual aid device and a urine containment bowl. The visual aid device has an adjustable support component; a yoke attached to the adjustable support component; a mirror surround rotatably attached to the yoke about a first rotational axis; a dual-sided mirror mounted to the mirror surround; and an independently repositionable focused-beam lamp mounted on the mirror surround. The urine containment bowl is attachable to the adjustable support component.

These and other features, aspects and advantages of the present invention will become better understood with reference to the following drawings, description, and claims.

BRIEF DESCRIPTION OF THE DRAWINGS

FIG. 1 is a perspective view of a self-catheterization assist device according to an embodiment of the present invention;

FIG. 2 is a perspective view thereof, in another position;

FIG. 5 is a front elevation view thereof, with bowl and screen removed;

FIG. 6 is a top plan view thereof;

FIG. 7 is a side elevation view thereof;

DETAILED DESCRIPTION OF THE INVENTION

Figure 3:
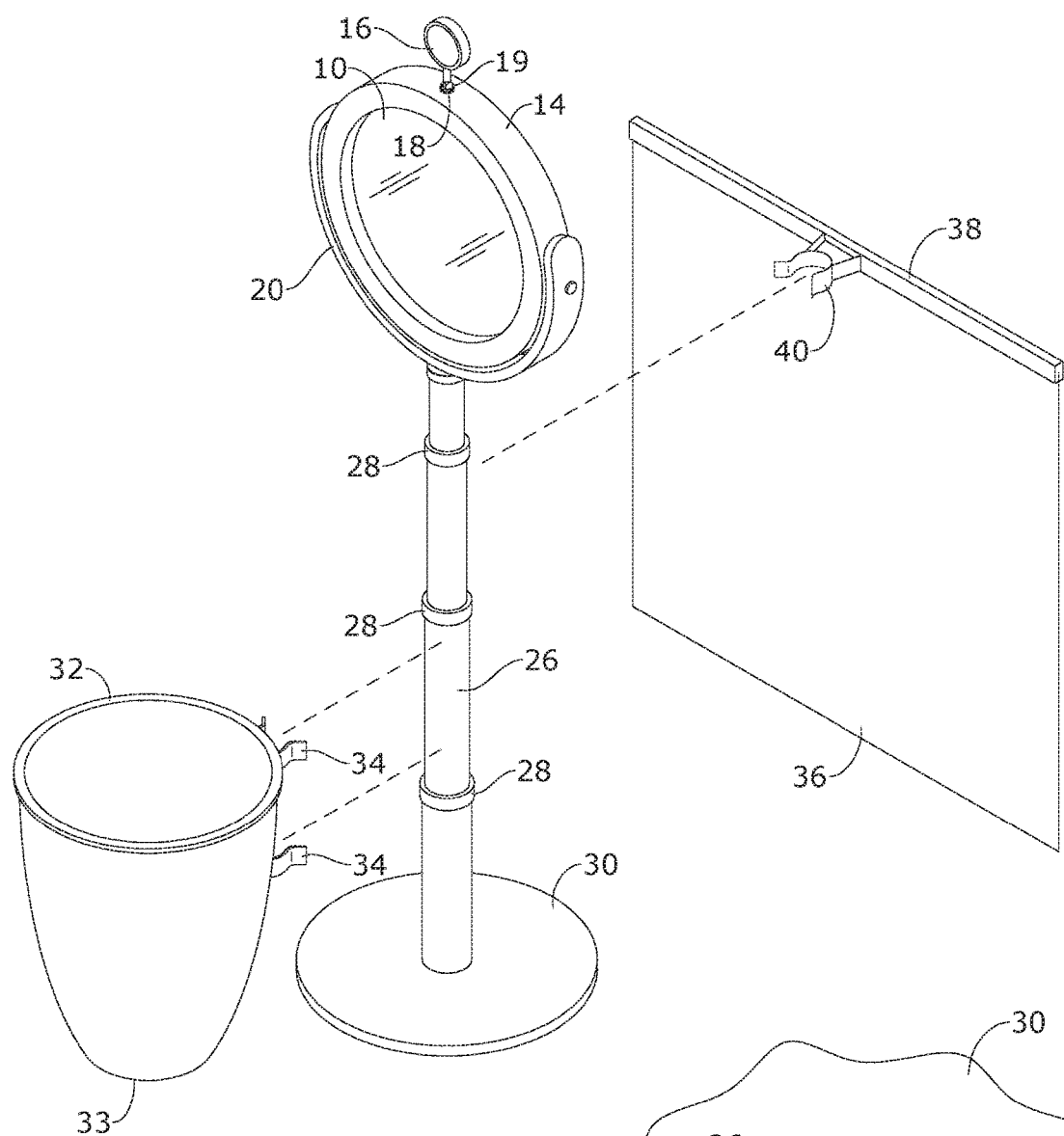
FIG. 3 is a partially exploded view thereof.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a self-catheterization assist device comprising at least one mirror held within a surround that is rotatably attached to a yoke about a first rotational axis. The yoke is further attached to an adjustable support component. The device may provide intense lighting to improve visibility, i.e., it is a visual aid device.

The yoke may be provided with one or more pivot points to adjust position and may have hardware to secure the position, such as adjustment screws.

The inventive device may be light and portable and may be manufactured in multiple sizes, e.g., small, medium, and large. Advantages of the inventive self-catheterization device include portability, independent set-up, clean technique (preventing cross contamination), improved personal hygiene, and infection control.

In some embodiments, the self-catheterization assist device comprises both a non-magnifying (flat or plane) mirror and a magnifying (concave) mirror for close inspection. Preferably, the device comprises a plano-concave mirror, i.e., with a flat surface and a concave surface.

In some embodiments, the adjustable support component comprises a base and pole. Preferably, the pole is a telescopic pole, for adjustability. The pole may further have hardware, such as position locks, to secure the pole in position. In some embodiments, the yoke may be rotatably attached to the pole about a second rotational axis orthogonal to the first rotational axis In some embodiments, the adjustable support component comprises a pair of bracket rods, each bracket rod also being attached to a leg bracket. Preferably, the rods are each telescopic bracket rods, for adjustability. The bracket rods may further have hardware to secure the rods in position, such as set screws.

In some embodiments, the inventive device may have intense, adjustable lighting provided by a light-emitting diode (LED) lighted mirror or mirror surround and/or a high intensity focused beam. For example, the mirror surround may be illuminated with light-emitting diodes. The mirror, mirror surround, or focused beam, or a combination thereof, may be rotatable and/or positionable. Preferably, the lighting sources are each rotatable and independently positionable (i.e., up, down, and around). For example, the high intensity focused beam lamp may be an independently repositionable focused-beam lamp with one or more pivot points to provide adjustability.

In some embodiments, the invention further comprises a urine containment component. The urine containment component may be in the form of a generally "V"-shaped bowl with a substantially flat bottom or base. The urine containment bowl may be suspended from one or more strap or cord between the user's legs to serve as container for liquids. The cords may be provided with cord stops to secure the bowl in position. Alternatively, the bowl may attach to the device with one or more clips. The user may choose whether to connect the bowl and may use it independently.

In some embodiments, the invention further comprises a screen to guard against splatter. The screen may be supported by a frame and the frame may be attached to the device with one or more clips. The user may choose whether to connect the screen and may use it independently.

Figure 4:
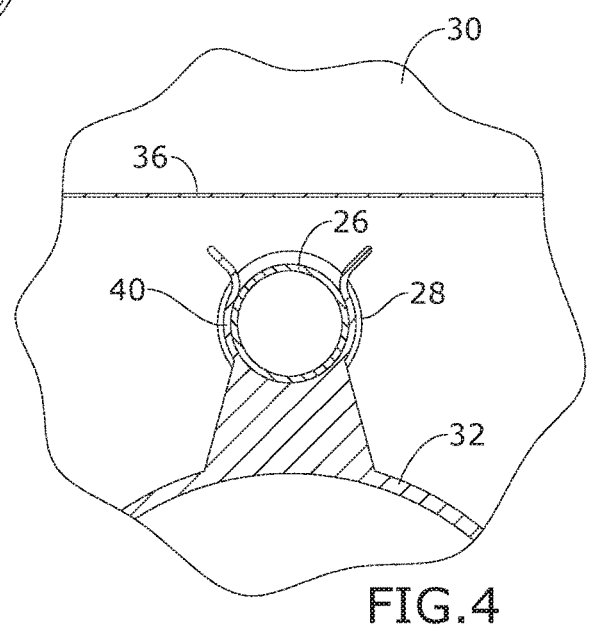
FIG. 4 is a sectional view thereof, taken along line 4-4 in FIG. 1.
Figure 8:
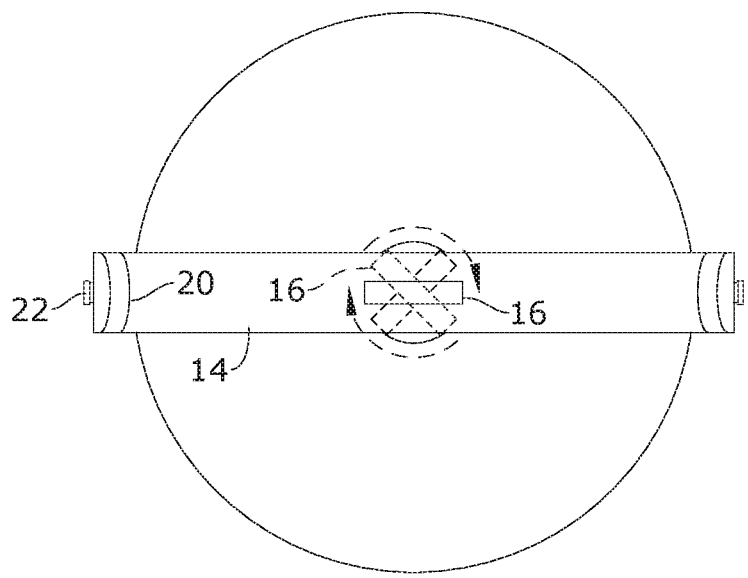
FIG. 8 is another top plan view thereof.
Figure 9:
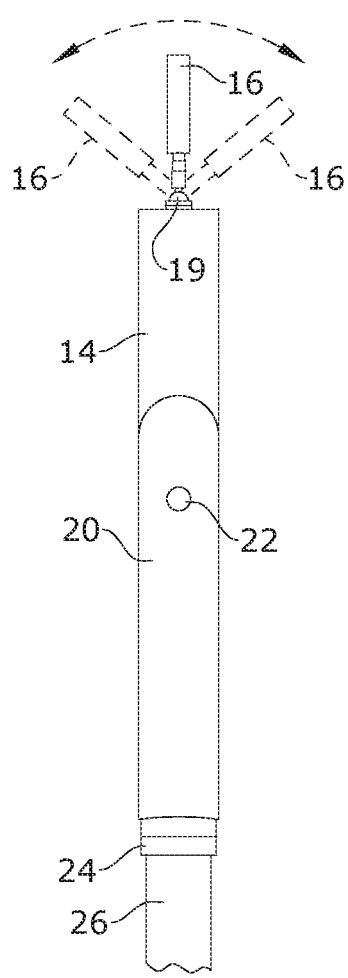
FIG. 9 is another side elevation view thereof.
Figure 10:
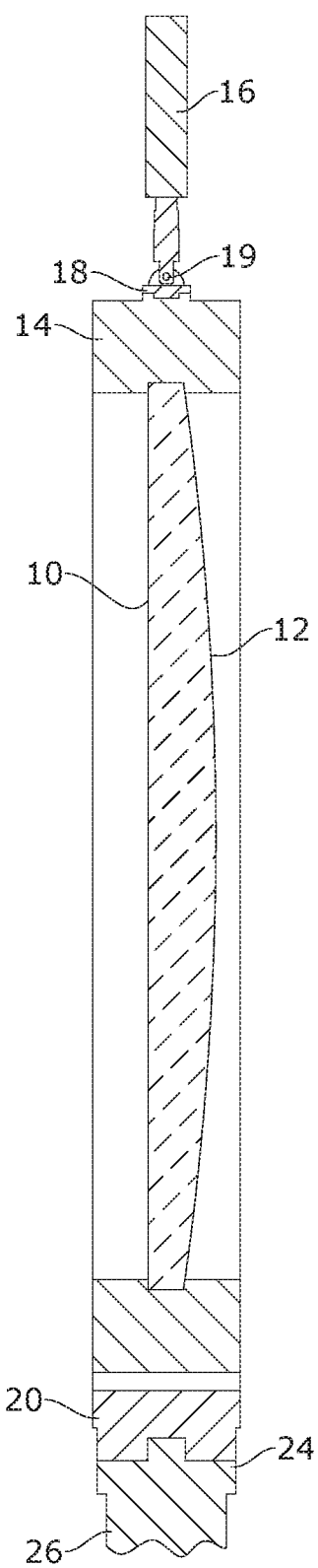
FIG. 10 is a sectional view thereof, taken along line 10-10 in FIG. 1.

Referring to FIGS. 1 through 15, FIGS. 1-10 illustrate a freestanding mirror kit with a removable catch bowl 32 and splatter screen 36. FIG. 1 shows an LED-lit mirror surround 14 holding a flat mirror 10, with a focused-beam LED light 16 supported on a telescoping light post 17 emerging from the top of the surround 14. The top LED light 16 may be repositioned by way of a top light horizontal pivot point 18 and a top light vertical pivot point 19. The surround 14, rotatably attached to a yoke 20, may be repositioned by way of angle adjustment screws 22 and may be rotated around a yoke pivot point 24. The surround 14 may be raised or lowered to optimize visibility using a telescoping pole 26 rising vertically from a base 30. The pole 26 may be kept in position with rod position locks 28. A catch bowl 32 with a flat bowl bottom 33 may be removably attached to the telescoping pole 26 with bowl clips 34. A splatter screen 36 suspended from a screen frame 38 may also be removably attached to the telescoping pole 26 with a screen clip 40. FIG. 2 shows a convex mirror 12 on the reverse side of the surround 14 from the flat mirror 10 and demonstrates the yoke 20 turning to show a convex mirror 12, with the top light post 17 extended. FIG. 3 illustrates the placement of or removal of the bowl 32 and the screen 36. FIG. 4 shows detail of the bowl 32 and screen 36 attached to the pole 26. FIG. 5, with the bowl 32 and screen 36 removed, illustrates how the height of the surround 14 may be adjusted with the telescoping pole 26 and how the height of the light 16 may be adjusted with the telescoping post 17. FIG. 6 illustrates that the yoke 20 and the focused beam light 16 may independently rotate 180 degrees. FIG. 7 shows that the mirror surround 14 angle may be adjusted within the yoke 20 when screws 22 are loosened. FIG. 8 illustrates that the focused beam light 16 may turn 180 degrees independently of the surround 14. FIG. 9 shows how the light 16 angle may be adjusted. FIG. 10 is a sectional view showing the flat mirror 10 on a first side and the convex mirror 12 on the opposite side within the surround 14, the yoke pivot point 24 connecting the yoke 20 to the pole 26, and the horizontal and vertical pivot points 18, 19 connecting the light 16 to the surround 14.

Figure 11:
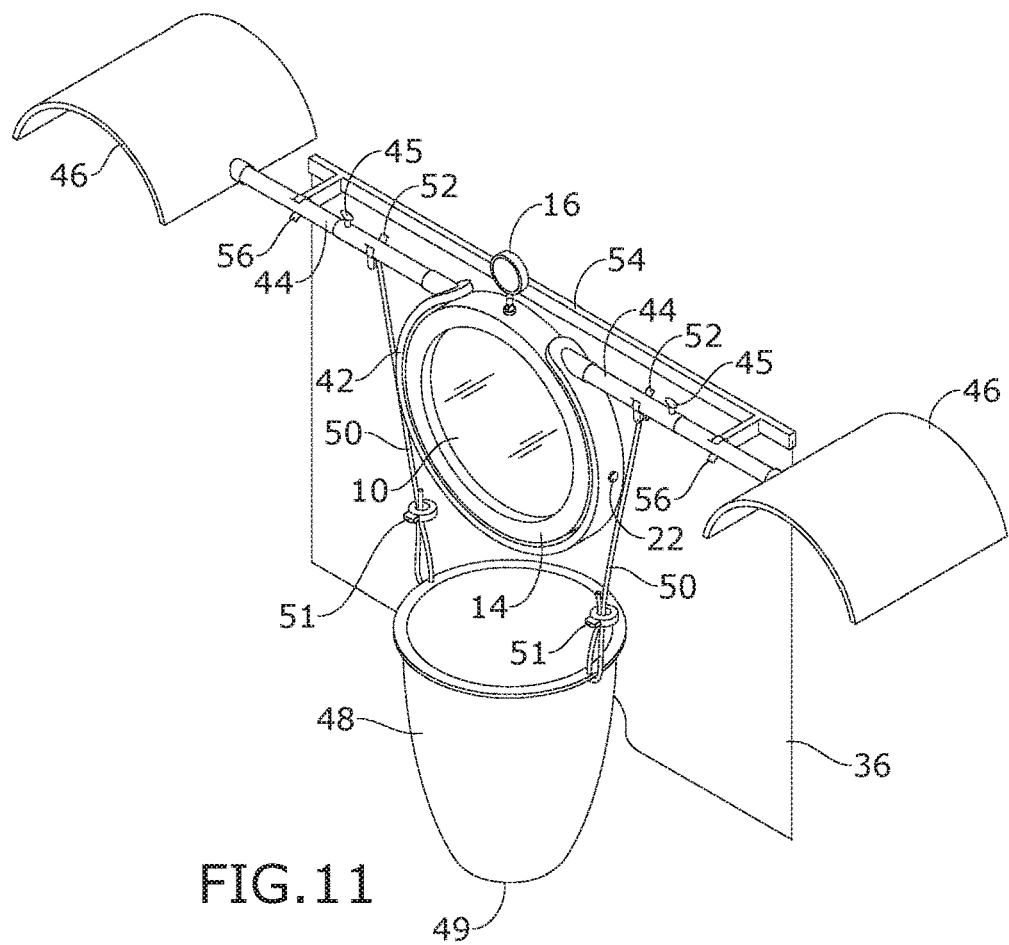
FIG. 11 is a perspective view of a self-catheterization assist device according to another embodiment of present invention.
Figure 12:
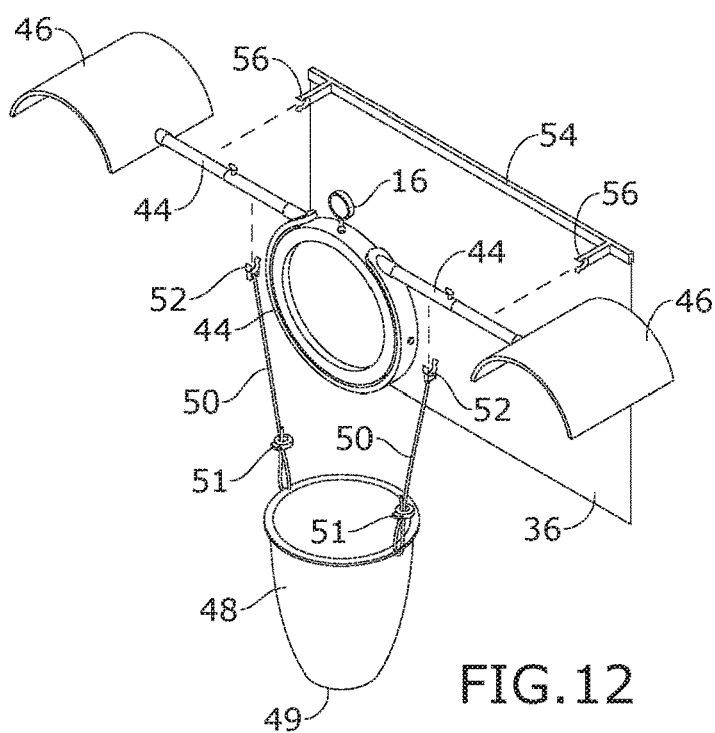
FIG. 12 is a partially exploded view thereof.
Figure 13:
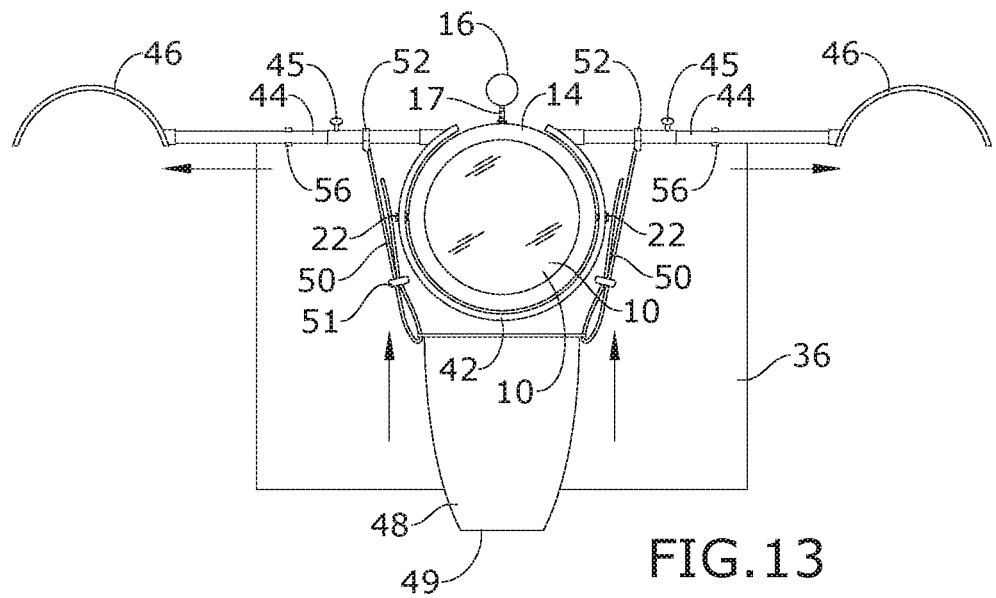
FIG. 13 is a front elevation view thereof.
Figure 14:
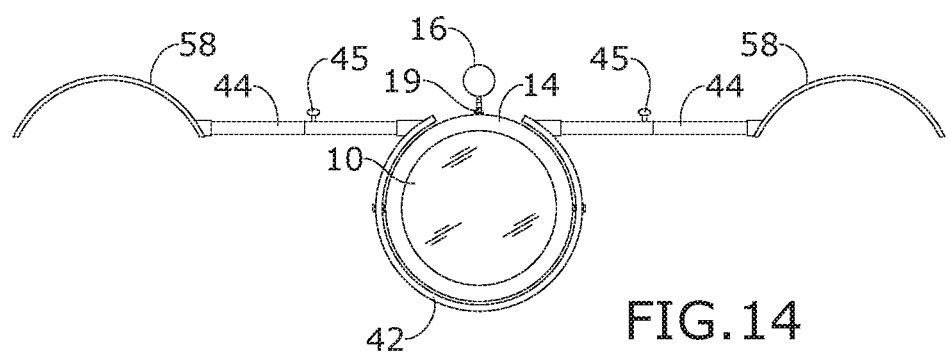
FIG. 14 is a front elevation view thereof, with bowl and screen removed.
Figure 15:
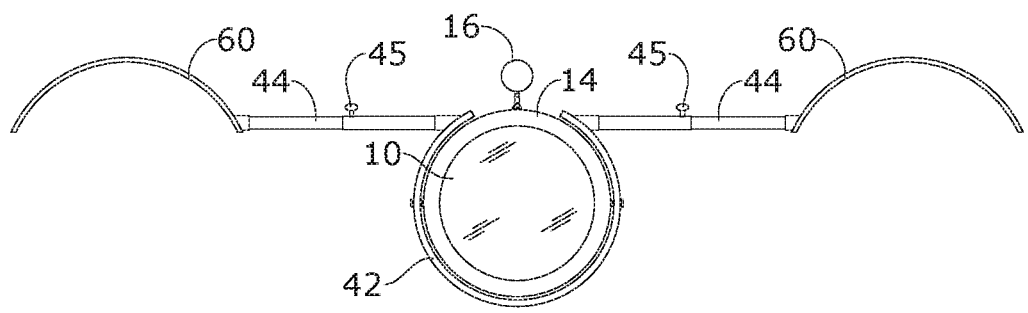
FIG. 15 is a front elevation view thereof.

FIGS. 11-15 illustrate another embodiment of the present invention comprising a leg-supported mirror kit with removable catch bowl 48 and splatter screen 36. FIG. 11 shows a flat, or plane, mirror 10 held within a LED-lit mirror surround 14 and rotatably attached to a yoke 42. The surround 14 may be adjusted within the yoke 42 using the angle adjustment screws 22. A focused-beam LED light 16 may be attached to the top of the surround 14 as shown. The yoke may be attached to two telescoping bracket rods 44, each rod 44 having a leg bracket or pad 46 (e.g., a padded leg bracket) at the distal end. The telescoping bracket rods 44 may be adjusted in length using bracket rod set screws 45. A splatter screen 36 may be suspended from a screen frame 54 and the screen frame 54 may be removably connected to the bracket rods 44 with frame clips 56. A catch bowl 48 with a flat bottom 49 may be removably suspended from the bracket rods 44 by a pair of bow cords 50 connected to the rods 44 with cord clips 52. The bow cords 50 may be adjustably held in place on the bowl 48 with cord stops 51. FIG. 12 illustrates placement of or removal of the splatter screen 36 and catch bowl 48. FIG. 13 illustrates how the length of the rods 44 may be adjusted and how the bowl 48 position may be adjusted by pulling the cords 50 through the stops 51. FIGS. 11 through 13 illustrate small pads 46. FIGS. 14 and 15 show the mirror device with the bowl 48 and screen 36 removed; FIG. 14 illustrates medium pads 58 and FIG. 15 illustrates large pads 60.

It should be understood, of course, that the foregoing relates to exemplary embodiments of the invention and that modifications may be made without departing from the spirit and scope of the invention as set forth in the following claims.

What is claimed is:

1. A self-catheterization assist device, comprising:
   a) an adjustable support component;
   b) a yoke attached to the adjustable support component;
   c) a radiant mirror surround rotatably attached to the yoke about a first rotational axis;
   d) a dual-sided mirror mounted to the radiant mirror surround;
   e) an independently repositionable focused-beam lamp mounted on the radiant mirror surround;
   f) a urine containment bowl positioned below the yoke and removably attached with at least one clip to the adjustable support component at a predetermined height; and
   g) a splatter screen removably attached to the adjustable support component such that the adjustable support component and the urine containment bowl are positioned between a user and the splatter screen;
   wherein the independently repositionable focused-beam lamp is vertically extendable from the radiant mirror surround, rotatable about a second rotational axis orthogonal to the first rotational axis, and pivotable about a horizontal pivot point.

2. The self-catheterization assist device of claim 1, wherein the dual-sided mirror is plano-concave.

3. The self-catheterization assist device of claim 1, wherein the radiant mirror surround is illuminated with light-emitting diodes.

4. The self-catheterization assist device of claim 1, wherein the adjustable support component is a telescopic pole to which the yoke is rotatably attached about the second rotational axis, said telescopic pole being attached to a base at an end distal to the yoke.

5. The self-catheterization assist device of claim 1, wherein the adjustable support component is a pair of telescopic bracket rods, each attached to the yoke at a first end and attached to a leg bracket at an other end.

6. A self-catheterization assist kit comprising:
   a) a visual aid device having:
      i) an adjustable support component;
      ii) a yoke attached to the adjustable support component;
      iii) a mirror surround rotatably attached to the yoke about a first rotational axis;
      iv) a dual-sided mirror mounted to the mirror surround; and
      v) an independently repositionable focused-beam lamp mounted on the mirror surround;
   b) a urine containment bowl; and
   c) a splatter screen;
   wherein the urine containment bowl further comprises at least one clip and is removably attached with the at least one clip to the adjustable support component below the yoke at a predetermined height and the splatter screen is removably attached to the adjustable support component such that the adjustable support component and the urine containment bowl are positioned between a user and the splatter screen.

7. The self-catheterization assist kit of claim 6, wherein the adjustable support component comprises a telescopic pole to which the yoke is rotatably attached about a second rotational axis orthogonal to the first rotational axis, said telescopic pole being attached to a base at an end distal to the yoke.

8. The self-catheterization assist kit of claim 6, wherein the adjustable support component is a pair of telescopic bracket rods, each attached to the yoke at a first end and attached to a padded leg bracket at an other end.

9. The self-catheterization device of claim 1, wherein the urine containment bowl is vertically adjustable relative to the mirror.

10. The self-catheterization device of claim 6, wherein the urine containment bowl is suspended from the at least one clip by a strap which is slidably adjustable and operative to position the urine containment bowl at the predetermined height.

* * * * *